United States Patent [19]

Alliger

[11] Patent Number: 5,389,679
[45] Date of Patent: Feb. 14, 1995

[54] METHOD OF TREATING SMALL MOUTH ULCERS WITH LACTIC ACID

[76] Inventor: Howard Alliger, 10 Ponderosa Dr., Melville, N.Y. 11747

[21] Appl. No.: 110,336

[22] Filed: Aug. 23, 1993

Related U.S. Application Data

[63] Continuation of Ser. No. 823,243, Jan. 21, 1992, abandoned.

[51] Int. Cl.⁶ .............................................. A61K 31/19
[52] U.S. Cl. .................................... 514/557; 514/925; 514/928
[58] Field of Search ............... 514/557, 925, 928, 738, 514/739

[56] References Cited

U.S. PATENT DOCUMENTS 4,221,794  9/1980  Simon ................................... 424/253
4,956,184  9/1990  Kross ................................... 424/661

FOREIGN PATENT DOCUMENTS 2134781  8/1984  United Kingdom ........ A61K 15/03

OTHER PUBLICATIONS

Chem Abstract 1202:12370h, Whitefield 1985.
Merck Manual, p. 1416, vol. 1, 1986.

*Primary Examiner*—Raymond J. Henley, III
*Assistant Examiner*—T. J. Criares
*Attorney, Agent, or Firm*—Henry D. Coleman; R. Neil Sudol

[57] ABSTRACT

The present invention relates to the surprising and unexpected discovery that a simple organic acid, lactic acid or its pharmaceutically compatible salts, may be used in a therapy for treating aphthous ulcers, including canker sores in humans.

The therapeutic method according to the present invention comprises exposing tissue suffering from an outbreak of aphthous ulcers to an effective amount of lactic acid.

19 Claims, No Drawings

METHOD OF TREATING SMALL MOUTH ULCERS WITH LACTIC ACID

This application is a continuation of Ser. No. 7/823,243, filed Jan. 21, 1992, now abandoned.

FIELD OF THE INVENTION

The present invention relates to a novel method of treating aphthous ulcers, including canker sores (aphthous stomotitis) in humans.

BACKGROUND OF THE INVENTION

Canker sores are recurrent, painful superficial oral ulcers that persist for several days to two weeks or more. Canker sores generally affect about 30% of the population. The lesions associated with canker sores are known technically as recurrent aphthous stomotitis (RAS) or aphthous ulcers. RAS may be "minor" or of a more serious "major" variant.

In general, canker sores or aphthous ulcers are characterized by small white spots associated with small ulcerations on the mucous membrane of the mouth. Up until recently, it was believed that these ulcerations were caused by a herpes virus or fungus, or after enteric use of broad spectrum antibiotics. Canker sores are one of the most common soft tissue diseases seen by the dentist. Canker sores may occur in any area of the oral cavity, in small groups or singularly.

Although there has been a great deal of research on the problem of canker sores, the cause and cure of these lesions remains obscure. Many mechanisms have been proposed including physic, allergic, microbial, diet, traumatic (stress), endocrine, hereditary and autoimmune.

Canker sores may affect patients of any age, but generally, those individuals between the ages of twenty and fifty years and especially women, are prone to outbreaks. In general, canker sores occur in women about twice as frequently as they occur in men. The frequency and severity of outbreaks vary remarkably between patients and within the same patient. In certain individuals, outbreaks occur once or twice a year, while in others, outbreaks may occur once or twice a month.

The outbreak of canker sore lesions is generally preceded by a prodromal period of several days during which period the patient experiences a burning or itching sensation in the oral mucosal area. The onset may also be preceded by a low grade fever and/or lymph node irritation. Upon onset, well defined ulcers form of approximately two to ten millimeters in diameter. These ulcers are generally surrounded by an intense erythematous halo with the base of the ulcer covered by a grayish necrotic tissue. Large, long standing ulcers are called major aphthae and involve the mucous glands, muscle and connective tissue. At this level, the disease may be quite painful and heal with scarring. In certain individuals, the ulcers never really disappear, with a new ulcer appearing as the older one heals.

Although there is a pyschosomatic component to the disease, and prominent feature is acute inflammation, a bacteria has also been isolated as a possible contributor to the disease process. This organism, *Streptococcus sanguis*, is found in the normal flora of the mouth. It is quite possible, that the above-described mechanisms which are associated with the disease may predispose an individual to bacterial infection by *Streptococcus sanguis*. There appears to be an immune response against this organism as well as to the epithelial tissue it infects. The ensuing inflammatory response causes localized damage to the host in the form of degeneration and necrosis.

In the acute form, several treatments are presently available including: tetracycline mouth rinses, topical cortisone and anesthetic mouth rinses. Systemic analgesics also may be administered. However, all of these therapies are fairly extreme and are generally reserved for multiple ulcers or major aphthae. All of these therapies should be carefully monitored.

Lactic acid, also known as 2-hydroxypropanoic acid, is a three carbon organic acid found in nature and the human body, is generally produced during the metabolism of sugars by lactic acid bacteria. Lactic acid may be found in sour milk, in molasses, in apples and other fruits, tomato juice, beer, wine, opium, ergot, foxglove and several higher plants. Lactic acid is generally prepared commercially by "lactic acid fermentation" of carbohydrates such as glucose, sucrose and lactose by *Bacillus acidi lacti* or related organisms such as *Lactobacillus delbrueckii* and *Lactobacillus bulgarius*, among others.

Therapeutically, lactic acid has been used as an acidulant, and in veterinary medicine, as a caustic, in dilute solutions to irrigate tissues and as an antiferment. Lactic acid is not known for its analgesic, anti-allergic or antimicrobial activity.

OBJECTS OF THE INVENTION

It is an object of the present invention to provide a novel therapeutic method for treating aphthous ulcers, including canker sores in humans.

It is a further object of the present invention to provide a method for treating apthous ulcers, including canker sores, in humans which is effective and inexpensive.

It is still a further object of the present invention to provide a method for treating aphthous ulcers, including canker sores in humans which is non-toxic and simple to administer.

It is still an additional object of the present invention to provide a prophylactic method for treating aphthous ulcers, including canker sores in humans.

These and other objects of the present invention may be readily gleaned from the description of the present invention which is set forth hereinbelow.

DESCRIPTION OF THE INVENTION

The present invention relates to the surprising and unexpected discovery that a simple organic acid, lactic acid or its pharmaceutically compatible salts, may be used in a therapy for treating aphthous ulcers, including canker sores in humans. It is particularly surprising that lactic acid may be used in the method according to the present invention in light of lactic acid's known uses.

The therapeutic method according to the present invention comprises exposing tissue suffering from an outbreak of aphthous ulcers to an effective amount of lactic acid.

In an additional method according to the present invention, tissue susceptible to outbreaks of aphthous ulcers is prophylactically treated with an effective amount of lactic acid on a daily basis.

Considering the varied etiology of and complicated chain of events leading to the disease, it is highly unexpected and quite surprising that a simple organic acid, such as lactic acid, already found in minute amounts in the mouth, would quickly and completely alleviate the disease associated with aphthous ulcers after exposure of the ulcers to effective amounts of lactic acid. In instances where tetracycline treatments (4 times daily) are needed to reduce healing time, lactic acid treatment stops the pain almost immediately with the first treatment and starts the healing process almost immediately.

Of great importance is the fact that the novel treatment of the present invention is inexpensive, does not need a prescription, is nontoxic and is simple to administer.

That lactic acid is an effective agent against aphthous ulcers, including canker sores, is particularly surprising in light of the fact that similar compounds such as citric acid, sorbic acid and boric acid do not work at all.

In the method according to the present invention, an effective amount of lactic acid or any one of its pharmaceutically compatible salts, for example, sodium or potassium lactate, preferably in solution, is administered to tissue suffering from aphthous ulcers. An effective amount of lactic acid is that concentration of lactic acid which will result in alleviated symptoms of aphthous ulcers, including canker sores.

While not being limited by way of theory, it is believed that the organic acid form of lactic acid, relative to the carboxylate salt form, appears to be more active in treating aphthous ulcers. Consequently, preferred compositions containing lactic acid for treating aphthous ulcers comprise an aqueous solution of lactic acid, in a concentration range of about 0.09 g to about 360 g. per liter (about 0.001M to about 4M or higher) having a pH less than about 6. The upper limit of concentration represents the practical limit of lactic acid solubility in an aqueous solution. The lower limit (0.001M) generally represents the minimum effective concentration of lactic acid (or one of its pharmaceutically acceptable salts) for treating aphthous ulcers. However, concentrations above or below this concentration range may be therapeutically active, and will depend upon the amount and type of pharmaceutical salt of lactic acid used as well as the final pH of the aqueous solution which determines the concentration of the carboxylic acid form of lactic acid in the solution. Concentrations of lactic acid of about 0.05 to about 1.5M are preferred.

Preferably, the lactic acid solution is administered at a pH ranging from about 2.0 to about 6.0, preferably about 2.2 to about 3.5 within the broader range, and the molar concentration of lactic acid, or its pharmaceutically compatible salt is preferably about 0.1 to about 1.5. Although it is possible to increase the activity of the aqueous solution by lowering the pH to below 2.0, it has been found that administering the lactic acid solution at a pH of below about 2.0 may result in the patient experiencing some physical or taste (sour) discomfort, which is believed to be associated with very low pH's. Likewise, it is also possible to administer the lactic acid solution according to the present invention at a pH of above about 6.0, but at pH's substantially above about 6.0, the activity of the lactic acid may fall dramatically.

In the method according to the present invention, lactic acid may be administered in any form, for example, as an aqueous solution, usually, for example, as a mouthwash, in addition to other aqueous forms or as solid forms, for example as chewable tablets, powders, gels or other solid pharmaceutical forms such as gums which dissolve or otherwise release lactic acid in the mouth. The form of administration may be varied according to the severity of the condition and the amount of lactic acid to be delivered to the affected tissue. The delivery form of lactic acid may also be determined by the age and compliance of the patient suffering from the aphthous ulcers.

In the prophylactic method for treating tissue susceptible to outbreaks of aphthous ulcers, an effective amount of lactic acid is used on a daily basis to prevent the outbreak of aphthous ulcers. Preferably, in this method, a dilute solution of aqueous lactic acid, preferably at a concentration ranging from about 0.001 to about 1.0M at a pH ranging from about 3.0 to about 5.0, most preferably about 3.0 to about 3.5–3.7 is used in mouthwash form to prevent the outbreak of aphthous ulcers prophylactically. In this method of the present invention, the mouthwash is used at least once daily for from 15 seconds to several minutes in order to prevent the outbreak of aphthous ulcers.

In addition to an effective amount of lactic acid, the compositions which can be used in the method according to the present invention may include additional agents which may facilitate the administration of lactic acid or otherwise enhance the beneficial effects that lactic acid has on aphthous ulcers. These additional agents may include, for example, wetting agents or surfactants such as sodium lauryl sulfate, certain polyethylene glycols, sulfates of long chain hydrocarbons, including cetyl sulfate, etc., higher fatty alcohol sulfates derived from coconut oil, among others, which are included for their surfactant action as well as the enhancement of delivery of lactic acid to the affected tissue. Other additives for use in the present invention may include pharmaceutically compatible antiseptics, disinfectants and preservatives for example, benzoic acid or any one of its pharmaceutically compatible analogs, as well as antimicrobial agents. A particularly preferred additive for use in the mouthwash aspect of the present invention is alcohol which may be added in an amount ranging from about 0.02 percent to about 30% by weight of the final concentration of the mouthwash. Pharmaceutically acceptable coloring agents or flavoring ingredients may also be included in the present invention.

To treat aphthous ulcers, lactic acid may be applied to the tissue at any time during the varied aphthous ulcer disease cycle. A preferred method is to is to rinse the mouth with a dilute solution of lactic acid, for example at a concentration of about 0.001 to about 0.1M at a pH of about 3.0 to about 4.5–5.0, preferably about 3.0 to about 3.5–3.7 for a period of about 15 seconds to a minute or two- like any mouthwash. After the initial mouthwash treatment, the affected area, and in particular, specific aphthous ulcer lesions, may be treated with a more concentrated acid (0.1 to about 1.0M or more generally at a pH of about 2.0 to 3.0, preferably 2.2 to 2.5) by applying the concentrated acid to the affected area with a saturated Q-tip, a wetted finger or other applicator. Applying any concentration of lactic acid to the affected area will help, but the higher the acid concentration, the faster and more effective will be the treatment.

The type and duration of treatment will generally depend on the severity of the disease and the condition of the tissue to be treated, with treatment regimens ranging from a singe treatment for as little as about 15 seconds, once a day treatment ranging from seconds to minutes or longer for several days to several treatments per day for several days or longer. The amount of lactic acid and the type of delivery vehicle will ultimately determine the duration of treatment of the affected tissue. However, for the usual case of aphthous ulcers, applying an effective concentration of lactic acid two or three times a day for a period ranging from about 15 seconds to several minutes or longer for two days is generally sufficient. Generally, using the method of treatment according to this invention, ulcerations will disappear without incident and the beneficial affect is seen almost instantly. In more extreme cases, application will generally be four or more times per day from about 15 seconds to several minutes or longer for several days or more. For the worse cases, the lactic acid treatments need be continued on a regular or near-regular basis, but almost always the pain associated with the ulcerations are nearly completely gone or greatly alleviated with the start of treatment.

EXAMPLES

The following examples are provided to illustrate the present invention and should not be construed to limit the scope of the invention of the present application in any way.

EXAMPLE 1

Lactic Acid Solution

A first aqueous solution of lactic acid (about 0.5M) is prepared by dissolving approximately 10 grams of 88% pure lactic acid (Sterling Chemical, Texas City, Tex., USA) in about 200 ml. of water. The pH is thereafter adjusted to about 2.2 with aqueous sodium hydroxide solution.

The above concentrated solution is thereafter diluted (10–15×) with water to provide a second aqueous solution with a final pH of 3.2–3.7.

EXAMPLE 2

Scores of individuals suffering from aphthous ulcers ranging from minor to major to chronic were treated with the compositions of example 1. The individuals were first treated with the dilute second aqueous solution by simply rinsing the mouth with the dilute solution for a period ranging from about 15 seconds to several minutes. Thereafter, the first concentrated aqueous solution was applied to cotton swabs, cloth, other applicator or the individuals finger and applied directly to the ulcers.

All of the above individuals exhibited reduced soreness almost immediately after only one treatment. Depending upon the severity of the condition, dramatic improvement was seen immediately, or after a few treatments. In the case of chronic aphthous ulcers improvement is steady, but should be performed on a regular basis.

This invention has been described in terms of specific embodiments set forth in detail herein, but it should be understood that these are by way of illustration and the invention is not necesarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

What is claimed is:

1. A method for treating aphthous ulcers of the mouth including canker sores, in humans, comprising topically exposing tissue suffering from an outbreak of aphthous ulcers to an effective amount of lactic acid or one of its pharmaceutically acceptable salts at a pH of less than about 6.0.

2. The method accoding to claim 1 wherein said lactic acid is administered in the form of an aqueous solution at a pH ranging from about 2.0 to about 4.5.

3. The method according to claim 2 wherein said aqueous solution comprises a concentration of lactic acid ranging from about 0.001M to about 4M.

4. The method according to claim 1 wherein said lactic acid is administered at a pH ranging from about 2.0 to about 3.5.

5. The method according to claim 1 wherein said lactic acid is administered at a pH ranging from about 2.2 to about 3.5.

6. The method according to claim 3 wherein said lactic acid ranges in concentration from about 0.1 to about 1.5M.

7. The method according to claim 1 wherein said pharmaceuticaly acceptable salt of lactic acid is selected from the group consisting of sodium lactate and potassium lactate.

8. The method according to claim 1 wherein said lactic acid or its salt is administered in combination with a surfactant.

9. The method according to claim 8 wherein said surfactant is sodium lauryl sulfate.

10. A method for treating aphthous ulcers including canker sores in humans comprising exposing tissue suffering from an outbreak of aphthous ulcers to an aqueous solution of lactic acid or one of its pharmaceutically acceptable salts in a concentration ranging from about 0.001 to about 0.1M at a pH of about 3.0 to about 5.0.

11. The method according to claim 10 wherein after said treatent with said aqueous solution, said tissue is treated a second time with a concentration of lactic acid ranging from about 0.1 to about 1.0M at a pH of about 2.0 to about 3.0.

12. The method according to claim 11 wherein said pH of said second concentration of lactic acid is about 2.2.

13. The method according to claim 11 wherein said second lactic acid concentration is administered in the form of an aqueous solution.

14. The method according to claim 10 wherein said pharmaceutically acceptable salt of lactic acid is selected from the group consisting of sodium lactate or potassium lactate.

15. The method according to claim 10 wherein said lactic acid or its salt is administered in combination with a surfactant.

16. The method according to claim 15 wherein said surfactant is sodium lauryl sulfate.

17. A method of prophylactically treating mucosal tissue of the mouth suspectible to an outbreak of aphthous ulcers, including canker sores, comprising exposing said tissue to an effective amount of lactic acid or one of its pharmaceutically acceptable salts at a pH of less than about 6.0.

18. The method according to claim 17 wherein said lactic acid is in the form of an aqueous solution at a concentration ranging from about 0.001 to about 1.0M and a pH ranging from about 3.0 to about 4.5.

19. The method according to claim 18 wherein said lactic acid is administered daily to said tissue.

* * * * *